United States Patent [19]

Kasat et al.

[11] Patent Number: 5,458,880
[45] Date of Patent: Oct. 17, 1995

[54] TRANSPARENT CLEAR COSMETIC STICK COMPOSITION CONTAING SODIUM SALTS OF METHYL CARBOXYL DERIVATIVES OF ETHOXYLATED LAURYL ALCOHOL

[75] Inventors: Radhakrishna B. Kasat, Belle Mead; Bhalchandra D. Moghe, Edison, both of N.J.

[73] Assignee: The Mennen Company, Morristown, N.J.

[21] Appl. No.: 54,302

[22] Filed: Apr. 30, 1993

[51] Int. Cl.$^6$ ........................................ A61K 7/00
[52] U.S. Cl. ............................... 424/401; 424/65
[58] Field of Search .......................... 424/401, 65, 76.1

[56] References Cited

U.S. PATENT DOCUMENTS

| | | |
|---|---|---|
| 3,444,091 | 5/1969 | Petraglia . |
| 4,154,816 | 5/1979 | Roehl et al. . |
| 4,268,498 | 5/1981 | Gedeon et al. . |
| 4,741,854 | 5/1988 | Krupa et al. . |
| 4,759,924 | 7/1988 | Luebbe et al. . |
| 4,851,147 | 7/1989 | Esposito et al. . |
| 4,948,578 | 8/1990 | Burger et al. . |
| 5,114,717 | 5/1992 | Kuznitz et al. . |
| 5,120,541 | 6/1992 | Macaulay et al. . |
| 5,128,123 | 7/1992 | Brewster et al. . |

FOREIGN PATENT DOCUMENTS

0450597A2  4/1991  European Pat. Off. .

*Primary Examiner*—José G. Dees
*Assistant Examiner*—Samuel Barts
*Attorney, Agent, or Firm*—Antonelli, Terry, Stout & Kraus

[57] ABSTRACT

Disclosed are transparent, clear cosmetic stick compositions of the type gelled with soaps such as sodium salts of saturated fatty acids, and containing an alcohol (e.g., propylene glycol) and water. The compositions include sodium salts of methyl carboxy derivatives of ethoxylated lauryl alcohol (e.g., sodium laureth-13 carboxylate) to improve transparency and clarity of the stick compositions. The soap gelling agent can be a mixture of sodium salts of fatty acids (e.g., saturated fatty acids) of carbon chain length $C_{12}$–$C_{22}$. The stick compositions can include deodorant active materials (such as fragrances, bacteriostats, bacteriocides, etc.) so as to provide transparent, clear deodorant stick compositions for application to axillary regions.

32 Claims, No Drawings

TRANSPARENT CLEAR COSMETIC STICK COMPOSITION CONTAING SODIUM SALTS OF METHYL CARBOXYL DERIVATIVES OF ETHOXYLATED LAURYL ALCOHOL

BACKGROUND OF THE INVENTION

The present invention relates to cosmetic stick compositions, i.e., cosmetic solid stick compositions such as deodorant solid stick compositions. More specifically, the present invention relates to cosmetic solid stick compositions containing an alcohol (for example, a monohydric alcohol, such as ethanol, or a polyhydric alcohol, such as propylene glycol) and water, and gelled with a soap (for example, an alkali metal salt of a saturated fatty acid). In particular, the present invention relates to transparent, clear cosmetic (deodorant) solid stick compositions with improved clarity and transparency, so as to achieve an improved appearance, and which retain such improved clarity and transparency over an extended period of time.

It has been desired to provide a soap-gelled, transparent, clear cosmetic stick composition, such as a soap-gelled, transparent, clear deodorant solid stick composition, which retains transparency and clarity over an extended period of time so as to have a long shelf life. It has also been desired to provide such a transparent, clear cosmetic stick composition, having a long shelf life, which avoids crystals forming in the stick.

U.S. Pat. No. 4,759,924, the contents of which are incorporated herein by reference in their entirety, discloses transparent, soap-gelled cosmetic stick compositions containing a polyhydric aliphatic alcohol having 2 to 6 carbon atoms; water; a soap gel-forming agent; and a hydro-alcoholic soluble emollient having the formula $R(OC_3H_6)_a(OC_2H_4)_bOH$, where R is either hydrogen or a hydrocarbon chain having from about 1 to 18 carbon atoms, and $a/(a+b) \leq 0.5$. This patent discloses that the polyhydric alcohol can illustratively be ethylene glycol or propylene glycol, and that mixtures of polyols can be used; and that illustratively the gel-forming agent can be the sodium, potassium and aluminum salts of fatty acids containing from about 14 to 18 carbon atoms. Preferred fatty acid soap gel-forming agents include sodium stearate, sodium palmitate, potassium stearate, potassium palmitate, sodium myristate and aluminum monostearate. Illustrative hydroalcoholic soluble emollients include PPG-5-Ceteth 20, PPG-3-Myreth-3, PEG-20-Laurate, PEG-6-32 and Polyoxamer 335.

U.S. Pat. No. 4,759,924 further discloses that the stick composition can include various optional ingredients, including conventional deodorant materials; and that the stick composition (gel stick) can be used by the consumer by rubbing the stick on the area of the body where application is desired. For example, in the case of a deodorant stick for underarm application, the stick is rubbed in the axillary area to apply the deodorant material.

While U.S. Pat. No. 4,759,924 describes a stick composition that it indicates is transparent, this patent does not disclose maintenance of transparency of the stick over an extended period of time.

U.S. Pat. No. 5,114,717 discloses a clear gel stick composition including a polyhydric alcohol and a soap, and further including an alkoxylate copolymer; the composition further includes fragrancing compounds, with the fragrancing compounds in the composition including from at most 25%, to 0.1%, total ester compounds by weight of the fragrance. This patent discloses that the alkoxylate copolymer has the formula $R_f[(C_2H_4O)_a(C_3H_6O)_b(C_2H_4O)_c(C_3H_6O)_d]_e[H]_g$, wherein R is selected from the group consisting of hydrogen, a $C_{10}$–$C_{22}$ fatty alkoxide chain, ethylene-diamine, and combinations thereof; a, b, c and d are independently selected integers ranging from 0 to 200 with a proviso that the sum of a, b, c and d is at least 5; e is an integer from 1 to 4; f is an integer from 0 to 1; and g is an integer from 0 to 4. This patent is based upon a discovery that certain types of fragrance components adversely effect clarity of soap-based cosmetic sticks, and that the fragrance components must be controlled for maintenance of stick clarity.

U.S. Pat. No. 5,128,123 discloses cosmetic compositions, in the form of sticks, which are clear and mild, containing (in addition to a polyhydric alcohol having from 2 to 6 carbon atoms and from 2 to 6 hydroxyl groups, water, and a soap) both (a) an alkoxylate copolymer, and (b) a clarifying agent (which is a basic amine) present in an effective amount to maintain clarity of the stick. The alkoxylate copolymer has a formula $[A-CH_2CH_2-A]_f[(C_2H_4O)_a(C_3H_6O)_b(C_2H_4O)_c(C_3H_6O)_d]_e[H]_g$, wherein A is nitrogen; a, b, c and d are independently selected integers ranging from 0 to 200 with the proviso that the sum of a, b, c and d is at least about 50; e is an integer from 1 to 4; f is an integer from 0 to 1; and g is an integer from 0 to 4. This patent discloses that the copolymer partially replaces the soap as a structurant in the stick. This patent further discloses that when f and e are 0 and 1, respectively, the structure described is a poly(ethylene oxide)(propylene oxide)(ethylene oxide) copolymer. This patent further discloses that the clarifying agent is preferably selected from amino alkanols having from 2 to 6 hydroxyl groups, particularly effective being the propanol amines.

U.S. Pat. No. 5,128,123 also defines what is meant by the term "clear" with respect to the stick composition described therein. Specifically, the term "clear" has its usual dictionary definition; thus, a clear cosmetic stick, like glass, allows for ready viewing of objects behind it. This patent contrasts clear cosmetic sticks with translucent cosmetic sticks, which allow light to pass through but causes the light to be so scattered that it will be impossible to clearly identify objects behind the translucent stick. This patent then goes on to define clear, translucent and opaque sticks based on transmittance of light of wavelength in the range of 400 to 900 nm through a sample 1 cm thick.

These definitions with respect to clear, translucent and opaque are also appropriate for the present invention. In addition, according to the present invention the term "transparent" is given its usual dictionary definition; that is, having the property of transmitting light therethrough so that bodies behind can be distinctly seen.

U.S. Pat. No. 4,268,498, the contents of which are incorporated herein by reference in their entirety, discloses a substantially clear cosmetic stick in which there are incorporated high levels of cosmetically active ingredients, the substantially clear cosmetic stick being non-irritating to the skin. The stick contains, as essential ingredients, polyoxyethylene (17–23)-glucose-fatty acid ester, polyoxyethylene (20–26) ether of a long-chain alcohol, polyoxypropylene (2–5) ether of a long-chain alcohol, sodium salt of a fatty acid, propylene glycol, lower alkyl ester of fatty acids, water, and a cosmetically active ingredient. This patent discloses that the cosmetically active ingredients include fragrances, sunscreens, skin conditioners, nail conditioners, deodorants and the like.

U.S. Pat. No. 5,120,541 discloses a transparent cosmetic stick composition having a lamellar structure and including an alcohol and soap, and optionally water, and further including a soap crystal growth inhibitor. This soap crystal growth inhibitor inhibits growth of soap crystals in the composition so as to achieve improved transparency, even in stick compositions containing relatively large amounts of monohydric alcohol. The soap crystal growth inhibitors include substituted or unsubstituted short-chain nonionics (a carbon chain length of less than $C_{24}$).

European Patent Application No. 450,597A2 discloses another transparent cosmetic gel stick composition. This composition consists essentially of an aliphatic polyhydric alcohol (such as propylene glycol); a soap (such as sodium stearate); a water-soluble emollient selected from the group consisting of (1) polyoxyethylene ethers of fatty alcohols, (2) polyoxyethylene/polyoxypropylene ethers of fatty alcohols, and (3) polyoxyethylene glycols; and water, the composition further including a water-dispersible emollient that is a polyoxyethylene ether of a branched chain fatty alcohol. This European patent document discloses that incorporation of the water-dispersible emollient in the composition including the polyhydric alcohol, soap, water and water-soluble emollient provides a gel solid stick composition that has better transparency to transmission of light as compared to the same composition not containing the water-dispersible emollient.

U.S. Pat. No. 4,154,816 discloses a transparent antiperspirant solid stick composition containing an antiperspirant metal compound, lower monohydric alcohols (such as ethanol and isopropanol), di- and/or trihydric alcohols (such as propylene glycol and/or lower polyglycols), propylene-/ethyleneglycol-polycondensate, dibenzaldehyde-mono-sorbitol acetal as a gelling agent, and mono-or dialkylol-amides of higher fatty acids. The propylene-/ethylene glycol-polycondensate has the formula $HO(C_2H_4O)_x(C_3H_6O)_yH$, where $y/(x+y)$ is from 0.6 to 1, and has an average molecular weight of at least 500. The composition of this patent uses an acetal, and not a soap, as the gelling agent; and contains, e.g., an acidic reacting antiperspirant compound, which would cause decomposition of the soap.

As seen in the foregoing, various cosmetic (e.g., deodorant) solid stick compositions, including compositions stated to be transparent, are known. However, it is still desired to provide cosmetic (e.g., deodorant) solid stick compositions containing an alcohol and water and gelled with a soap, which are clear and transparent, and retain their clarity and transparency for relatively long periods of time. Moreover, it is still desired to provide such cosmetic solid stick compositions, having various cosmetically active ingredients (such as deodorant active ingredients) incorporated therein, that have such clarity and transparency and maintain such clarity and transparency.

SUMMARY OF THE INVENTION

Accordingly, it is an object of the present invention to provide a cosmetic stick composition (e.g., a cosmetic solid stick composition) that is clear and transparent, and that is compatible (e.g., maintains such clarity and transparency) when cosmetically active materials (such as deodorant active materials, including fragrances, bacteriostats, and bactericides, sunscreens, etc.) are incorporated therein.

It is a further object of the present invention to provide a cosmetic solid stick composition that is clear and transparent when having cosmetically active materials incorporated therein.

It is a further object of the present invention to provide a transparent, clear stick composition, which is transparent and clear even when a cosmetically active material is incorporated therein, and which maintains clarity and transparency for relatively long periods of time (so as to have a relatively long shelf life).

It is a further object of the present invention to provide a transparent, clear cosmetic stick composition containing alcohol and water, and gelled by a soap (such as alkali metal salts of fatty acids), which maintains clarity and transparency for long periods of time.

It is a further object of the present invention to provide transparent, clear deodorant solid stick compositions having deodorant active materials incorporated therein, which can be applied, e.g., to axillary regions of the body to reduce or avoid malodor.

The foregoing objects are achieved, according to the present invention, by incorporating sodium salts of methyl carboxy derivatives of ethoxylated lauryl alcohol in a stick composition containing alcohol and water and gelled with a soap (e.g., a metal salt of a fatty acid). For example, these objects are achieved by incorporating sodium salts of methyl carboxy derivatives of ethoxylated lauryl alcohol in a stick composition containing polyhydric alcohol and water, and gelled with sodium salts of fatty acids, e.g., sodium salts of saturated fatty acids having carbon chain length $C_{12}$–$C_{22}$. The sodium salts of methyl carboxy derivatives of ethoxylated lauryl alcohol are included in the stick composition in an effective amount so as to provide clarity and transparency to the stick composition, and maintain such clarity and transparency. Illustratively, a transparent, clear cosmetic stick composition according to the present invention includes propylene glycol and water, gelled with sodium salts of long-chain saturated fatty acids of carbon chain length $C_{12}$–$C_{22}$, and further includes sodium laureth-13 carboxylate (CTFA (Cosmetics, Toiletry and Fragrance Association, Inc.) name) as a sodium salt of methyl carboxy derivative of ethoxylated lauryl alcohol. By incorporating the above-referred-to sodium salts of methyl carboxy derivatives of ethoxylated lauryl alcohol in the cosmetic stick composition, an improved appearance of transparency and clarity is achieved, and an improved appearance is maintained for an extended period of time so as to provide a product also having improved shelf life.

Preferably, the cosmetic stick composition according to the present invention contains the sodium salts of methyl carboxy derivatives of ethoxylated lauryl alcohol in an amount of 1%–8% by weight of the total weight of the composition, more preferably 3%–8% by weight of the topical weight of the composition, in order to provide a stick with the most satisfactory transparency and clarity.

The transparent, clear stick compositions according to the present invention can include various active materials, including sunscreens, deodorant active materials, etc. As would be appreciated, the product formed would be a sun protection stick, deodorant stick, etc., depending upon the active material incorporated in the cosmetic solid stick composition. As for various active materials which can be incorporated in the stick composition according to the present invention, see U.S. Pat. No. 5,128,123, the contents of which are incorporated herein by reference in their entirety.

A specific use of the stick composition according to the present invention is as a transparent, clear deodorant stick composition. Such stick composition would include (in addition to the base composition of propylene glycol, water, soap (e.g., sodium salt of long-chain saturated or unsaturated fatty acids of carbon chain length $C_{12}$ to $C_{22}$), and sodium salt of methyl carboxy derivative of ethoxylated lauryl alcohol) a deodorant active material such as a bacteriostat and/or a bacteriocide and/or a fragrance.

The compositions according to the present invention can include additional materials conventionally included in cosmetic stick compositions, as long as such additional materials do not disadvantageously affect the transparency and clarity of the final composition. Various materials incorporated in stick compositions are disclosed in U.S. Pat. No. 4,759,924, the contents of which have previously been incorporated herein by reference in their entirety. The additional materials can include, illustratively, polyols, fatty alcohols, alkanolamide, color (dyes), essential oils, and soluble inorganic salts of sodium or potassium.

Accordingly, by the present invention, which incorporates sodium salts of methyl carboxy derivatives of ethoxylated lauryl alcohol in the soap-gelled solid stick composition containing alcohol and water, a solid stick composition is provided that is transparent and clear, and retains its clarity and transparency over relatively long periods of time.

DETAILED DESCRIPTION OF THE INVENTION

While the invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Throughout the present specification, where compositions are described as including or comprising specific components or materials, it is contemplated by the inventors that compositions of the present invention also consist essentially of, or consist of, the recited components or materials. Accordingly, throughout the present disclosure any described composition of the present invention can consist essentially of, or consist of, the recited components or materials.

The present invention contemplates clear and transparent cosmetic stick compositions (for example, clear and transparent deodorant solid stick compositions) containing alcohol and water, and gelled with salts (soaps) of saturated or unsaturated fatty acids (that is, the composition further containing salts of saturated or unsaturated fatty acids, as gelling agents for the alcohol and water), the compositions further including sodium salts of methyl carboxy derivatives of ethoxylated lauryl alcohol. Illustratively, sodium laureth-13 carboxylate can be incorporated in the cosmetic stick composition to achieve the desired objectives. Another name for sodium laureth-13 carboxylate is "Surfine WLL" (Finetex, Inc.).

The alcohol included in the solid stick composition of the present invention can be a monohydric and/or polyhydric alcohol (for example, ethanol as a monohydric alcohol, and propylene glycol and dipropylene glycol as polyhydric alcohol). The alcohol can be a mixture of alcohols, including a mixture of monohydric and polyhydric alcohols, or a mixture of monohydric alcohols or a mixture of polyhydric alcohols. Various polyhydric alcohols which can be used in soap-gelled alcohol-and water-containing stick compositions are described in U.S. Pat. No. 4,759,924, the contents of which have previously been incorporated herein by reference in their entirety, and can also be used in the present invention.

A necessary component of the cosmetic stick composition according to the present invention is a soap gel-forming agent. Sodium salts of fatty acids of carbon chain length $C_{12}$–$C_{22}$, e.g., sodium salts of saturated fatty acids having the above-mentioned carbon chain length, can be utilized as the gel-forming agent. Preferred gel-forming agents according to the present invention include sodium salts (that is, soaps) of relatively long-length-carbon-chain saturated fatty acids (for example, sodium salts of saturated fatty acids having carbon chain lengths of $C_{20}$–$C_{22}$). The fatty acid portions of the soap can include a mixture of different saturated fatty acids of carbon chain length in the range $C_{12}$–$C_{22}$, preferably including some $C_{20}$ and $C_{22}$. By utilizing such relatively long chain length fatty acids, a product is provided having a relatively high melting temperature, and, correspondingly, relatively greater stability.

Preferred gel-forming agents according to the present invention include mixtures of sodium fatty acid soaps, having different fatty acid portions. For example, the soap gel-forming agent can be a mixture of sodium laurate, sodium myristate, sodium palmitate, sodium stearate, sodium arachidate, and sodium behenate, with the sodium fatty acid soaps respectively having the following distribution:

| Fatty Acid Soap | % (by weight, of the soap mixture) |
| --- | --- |
| Sodium laurate | 2% |
| Sodium myristate | 4–7% |
| Sodium palmitate | 35–44% |
| Sodium stearate | 31–44% |
| Sodium arachidate | 7–9% |
| Sodium behenate | 8–10% |

This mixture of sodium fatty acid soaps, having the desired distribution, can be provided in any number of ways known in the art. For example, pure sodium laurate, sodium myristate, etc., can be mixed together in desired proportions. Or different mixtures of sodium fatty acid soaps (for example, commercial grade sodium stearate, containing sodium stearate, sodium palmitate, etc., and another mixture of sodium fatty acid soaps) can be combined to provide the desired distribution.

The foregoing fatty acid soap distribution of the soap gel-forming agent is illustrative and not limiting of the present invention.

As described previously, the transparent, clear cosmetic stick composition according to the present invention should include an effective amount of the sodium salt of methyl carboxyl derivative of ethoxylated lauryl alcohol, so as to provide a transparent, clear cosmetic stick composition and maintain such transparency and clarity. Illustratively, and not limiting, the composition can contain 1%–8% by weight of such sodium salts. Illustratively, and not limiting, the cosmetic stick composition according to the present invention can also include the following amounts (in percent by weight of the total weight of the composition) of other components:

Alcohol (e.g., propylene glycol): 55–80%

Water: 9–25%

Soap: 4–10%

Note that as the amount of water included in the composition increases, the solidified composition has a tendency to become more hazy.

As stated previously, other materials can be included in the transparent, clear stick compositions according to the present invention, and include various cosmetically active materials. Thus, materials such as deodorant active materials (including fragrances), sunscreens, skin conditioners, nail conditioners, and the like, can be included in the composition, provided that they do not unsatisfactorily affect clarity and transparency and, where appropriate, can be applied to the human body.

As indicated previously, compositions according to the present invention have use as underarm deodorant compositions (e.g., by application to axillary regions of the human body), when having deodorant active materials incorporated in the composition. Various deodorant active materials which can be included in compositions according to the present invention are described in U.S. Pat. No. 4,759,924, and include bacteriostats and fragrances (e.g., perfumes), and bactericides, among others. For example, a deodorant material useful in the present compositions is 2-4-4'-trichloro-2'-hydroxydiphenyl ether (CTFA name: Triclosan).

Other ingredients such as dyes, pigments, coloring agents, etc., which do not disadvantageously affect the clarity and transparency of the solid stick compositions of the present invention, can be incorporated in the soap-gelled compositions of the present invention.

The compositions according to the present invention are manufactured by processing techniques conventional in the art. Specifically, the solid components of the composition are melted and then the components are mixed. Preferably, the fragrance (if any) is added last, with the previously mixed components being cooled to a lower temperature (while still maintaining a liquid) prior to adding the fragrance, so as to limit any volatilization of the fragrance. While still in the liquid state, the composition is filled in a dispensing package (as conventional in the art) and then cooled to solidify the product in the package.

The compositions according to the present invention are utilized by conventional techniques. For example, when utilizing compositions according to the present invention as an axillary deodorant solid stick, having deodorant active materials (such as Triclosan and/or a fragrance) incorporated therein, the solid stick product is elevated out of a dispensing package so as to expose the stick product and the exposed portion of the stick product is then rubbed against, e.g., the axillary region of the human body so as to deposit the deodorant active materials in the axillary region.

While in the foregoing the present invention has been described in terms of a deodorant solid stick composition for use in axillary regions, the present invention is not so limited, and the cosmetic stick composition according to the present invention has various uses depending on the active material incorporated therein, including as a deodorant for other parts of the body, sunscreen, insect repellant, etc.

In the following, specific examples of compositions within the scope of the present invention will be set forth. Of course, these specific examples are illustrative of the present invention and are not limiting.

In the following examples, the stated percentages are percentages by weight, of the stated component, relative to the total weight of the composition. The names utilized are the CTFA names for the ingredients, where applicable.

Also, in the following examples, soap gel-forming agents "A" and "B" are referred to. Each of these soap gel-forming agents is mixtures of different sodium fatty acid soaps, with different fatty acid portions, as set forth in the following:

| Fatty Acid Soap | % (by weight, of the soap mixture) |
|---|---|
| Soap Gel-Forming Agent A: | |
| Sodium laurate | 2% |
| Sodiura myristate | 4–7% |
| Sodium palmitate | 35–44% |
| Sodium stearate | 31–44% |
| Sodium arachidate | 7–9% |
| Sodium behenate | 8–10% |
| Soap Gel-Forming Agent B: | |
| Sodium laurate | 1% |
| Sodium myristate | 4–10% |
| Sodium palmitate | 20–30% |
| Sodium stearate | 25–42% |
| Sodium arachidate | 15–18% |
| Sodium behenate | 17–20% |

EXAMPLE I

| Ingredients | |
|---|---|
| Soap Gel-Forming Agent B | 5.00 |
| Propylene glycol | 73.29 |
| Triclosan | 0.25 |
| Deionized water | 14.56 |
| Sodium laureth-13 carboxylate | 5.5 |
| Fragrance | 1.00 |
| Color | 0.4 |

The composition of Example I was manufactured using the following steps. Initially, propylene glycol was melted. Thereafter, the Triclosan was added and mixed into the propylene glycol until dissolved. The soap gel-forming agent B was then added, and mixed into the propylene glycol/Triclosan mixture until dissolved. Thereafter, the sodium laureth-13 carboxylate was added and dissolved in the aforementioned mixture. Then the water was added and mixed, the resulting mixture being cooled but being maintained as a liquid. Then, color and fragrance were added. Thereafter, the resulting mixture was filled into solid stick packages, and cooled to a solid in the package.

EXAMPLE II

| Ingredients | |
|---|---|
| Soap Gel-Forming Agent A | 5.0 |
| Propylene glycol | 74.00 |
| Triclosan | 0.25 |
| Deionized water | 14.56 |
| Sodium laureth-13 carboxylate | 5.00 |
| Fragrance | 1.00 |
| Color | 0.19 |

EXAMPLE III

| Ingredients | |
|---|---|
| Soap Gel-Forming Agent B | 6.00 |
| Propylene glycol | 70.25 |
| Triclosan | 0.25 |
| Deionized water | 17.31 |

-continued

| Ingredients | |
|---|---|
| Sodium laureth-13 carboxylate | 2.00 |
| PPG-2-Ceteareth-9 | 3.0 |
| Fragrance | 1.00 |
| Color | 0.19 |

EXAMPLE IV

| Ingredients | |
|---|---|
| Soap Gel-Forming Agent B | 6.00 |
| Propylene glycol | 70.25 |
| Triclosan | 0.25 |
| Deionized water | 14.31 |
| Sodium laureth-13 carboxylate | 5.00 |
| PPG-2-Ceteareth-9 | 3.00 |
| Fragrance | 1.00 |
| Color | 0.19 |

The foregoing Examples III and IV illustrate incorporation of an Eumulgin compound (specifically, Eumulgin L, having CTFA name: PPG-2–Ceteareth-9) in a transparent, clear stick composition containing a sodium salt of a methyl carboxy derivative of ethoxylated lauryl alcohol. Incorporation of Eumulgin compounds in soap-gelled stick compositions containing water and an alcohol are disclosed in the application of Bhalchandra D. Moghe and Radhakrishna B. Kasat for "Transparent Clear Stick Composition" (attorney docket No.: 851.31603X00), filed concurrently herewith, the contents of which are incorporated herein by reference in their entirety. Various Eumulgin compounds as described in this co-pending application can be incorporated in compositions containing sodium salts of methyl carboxy derivatives of ethoxylated lauryl alcohol according to the present invention.

While we have shown and described several embodiments in accordance with the present invention, it is understood that the same is not limited thereto, but is susceptible of numerous changes and modifications as known to those skilled in the art. Therefore, we do not wish to be limited to the details shown and described herein, but intend to cover all such changes and modifications as are encompassed by the scope of the appended claims.

We claim:

1. A transparent, clear cosmetic stick composition comprising an alcohol and water, and gelled with a salt of a fatty acid, the composition further including a sodium salt of a methyl carboxy derivative of ethoxylated lauryl alcohol as an agent to provide the composition as a transparent, clear composition, the sodium salt of a methyl carboxy derivative of ethoxylated lauryl alcohol being included in the composition in an effective amount to provide a transparent, clear stick composition.

2. The composition as defined in claim 1, wherein the sodium salt of a methyl carboxy derivative of ethoxylated lauryl alcohol is sodium laureth-13 carboxylate.

3. The composition as defined in claim 2, wherein the sodium laureth-13 carboxylate is included in the composition in an amount of 1%–8% by weight of the total weight of the composition.

4. The composition as defined in claim 1, wherein the alcohol is propylene glycol, and the salt of a fatty acid is a sodium salt of fatty acids having carbon chain lengths of $C_{12}$–$C_{22}$.

5. The composition as defined in claim 4, wherein the sodium salt of a methyl carboxy derivative of ethoxylated lauryl alcohol is sodium laureth-13 carboxylate.

6. The composition as defined in claim 5, wherein the sodium laureth-13 carboxylate is included in the composition in an amount of 1%–8% by weight of the total weight of the composition.

7. The composition as defined in claim 6, further including deodorant materials, such that the composition is a transparent, clear deodorant stick composition for application to axillary regions.

8. The composition as defined in claim 7, wherein the deodorant materials include fragrances.

9. The composition as defined in claim 8, wherein the deodorant materials further include a bacteriostat or bacteriocide.

10. The composition as defined in claim 2, further including deodorant materials, such that the composition is a transparent, clear deodorant stick composition for application to axillary regions.

11. The composition as defined in claim 1, wherein the composition further includes at least one Eumulgin compound.

12. The composition as defined in claim 11, wherein the sodium salt of a methyl carboxy derivative of ethoxylated lauryl alcohol is sodium laureth-13 carboxylate.

13. The composition as defined in claim 12, wherein said at least one Eumulgin compound is PPG-2-ceteareth-9.

14. The composition as defined in claim 13, further including deodorant materials, such that the composition is a transparent, clear deodorant stick composition for application to axillary regions.

15. The composition as defined in claim 1, wherein the alcohol includes polyhydric alcohols.

16. The composition as defined in claim 15, wherein the polyhydric alcohols include a mixture of polyhydric alcohols.

17. The composition as defined in claim 16, wherein the mixture of polyhydric alcohols includes propylene glycol and dipropylene glycol.

18. The composition as defined in claim 17, wherein the sodium salt of a methyl carboxy derivative of ethoxylated lauryl alcohol is sodium laureth-13 carboxylate.

19. The composition as defined in claim 1, wherein the alcohol includes monohydric alcohols.

20. The composition as defined in claim 19, wherein the sodium salt of a methyl carboxy derivative of ethoxylated lauryl alcohol is sodium laureth-13 carboxylate.

21. The composition as defined in claim 1, consisting essentially of said alcohol, water, salt of a fatty acid and sodium salt of a methyl carboxy derivative of ethoxylated lauryl alcohol.

22. The composition as defined in claim 1, further including deodorant materials, such that the composition is a transparent, clear deodorant stick composition.

23. The composition as defined in claim 22, consisting essentially of said alcohol, water, salt of a fatty acid, deodorant materials and sodium salt of a methyl carboxy derivative of ethoxylated lauryl alcohol.

24. The composition as defined in claim 1, wherein the sodium salt of a methyl carboxy derivative of ethoxylated lauryl alcohol is included in the composition in an amount sufficient to maintain said transparent, clear stick composition.

25. The composition as defined in claim 1, wherein the sodium salt of a methyl carboxy derivative of ethoxylated lauryl alcohol is included in the composition in an amount of 3%–8% by weight of the total weight of the composition.

26. The composition as defined in claim 25, wherein the sodium salt of a methyl carboxy derivative of ethoxylated lauryl alcohol is sodium laureth-13 carboxylate.

27. The composition as defined in claim 1, wherein the salt of a fatty acid is a mixture of sodium salts of fatty acids having carbon chain lengths of $C_{12}$–$C_{22}$, at least some of the fatty acids having at least one of $C_{20}$ and $C_{22}$ carbon chain length.

28. The composition as defined in claim 27, wherein the mixture of sodium salts of fatty acids is a mixture of sodium laurate, sodium myristate, sodium palmitate, sodium stearate, sodium arachidate and sodium behenate.

29. The composition as defined in claim 28, wherein the mixture of sodium salts of fatty acids has a distribution as follows:

| Fatty acid soap | % (by wt. of the mixture) |
|---|---|
| sodium laurate | 2% |
| sodium myristate | 4–7% |
| sodium palmitate | 35–44% |
| sodium stearate | 31–44% |
| sodium arachidate | 7–9% |
| sodium behenate | 8–10% |

30. The composition as defined in claim 1, containing, in % by weight of the total weight of the composition, 55–80% of said alcohol, 2–25% water, and 4–10% of said salt of a fatty acid.

31. The composition as defined in claim 30, wherein the sodium salt of a methyl carboxy derivative of ethoxylated lauryl alcohol is included in the composition in an amount of 1%–8% by weight of the total weight of the composition.

32. The composition as defined in claim 31, wherein the sodium salt of a methyl carboxy derivative of ethoxylated lauryl alcohol is sodium laureth-13 carboxylate.

* * * * *